United States Patent [19]

Nardi et al.

[11] Patent Number: 5,030,094
[45] Date of Patent: Jul. 9, 1991

[54] COUPLING DEVICE FOR DENTAL PROSTHESES

[76] Inventors: Ezio Nardi, Via Friuli Venezia Giulia 14/3, 40100 Bologna; Gianni Ronconi, Via Porrettana 522, 40033 Casalecchio di Reno (Province of Bologna, both of Italy

[21] Appl. No.: 506,517

[22] Filed: Apr. 5, 1990

Related U.S. Application Data

[63] Continuation of Ser. No. 64,481, Jun. 22, 1987.

[30] Foreign Application Priority Data

Jun. 24, 1986 [IT] Italy ................................. 4916/86[
Jun. 5, 1987 [IT] Italy ................................. 4891/87[

[51] Int. Cl.⁵ .............................................. A61C 13/28
[52] U.S. Cl. ..................................... 433/169; 433/220; 433/181
[58] Field of Search ............... 433/169, 170, 220, 172, 433/173, 177, 180, 181, 182, 183, 192

[56] References Cited

U.S. PATENT DOCUMENTS 3,641,670  2/1972  Karageorge ..................... 433/180
4,362,511 12/1982  Jacklich ............................ 433/220
4,571,185  2/1986  Rota ................................. 433/173
4,626,213 12/1986  Shiner et al. ..................... 433/173

FOREIGN PATENT DOCUMENTS 1004861  4/1952  France ............................ 433/220
0466420 10/1951  Italy ............................... 433/220
0597843  4/1978  Switzerland ..................... 433/173

Primary Examiner—John J. Wilson
Assistant Examiner—Adriene B. Lepiane
Attorney, Agent, or Firm—Guido Modiano; Albert Josif

[57] ABSTRACT

The coupling device comprises a substantially spherical male element, rigidly associated with a support member, in turn adapted to be rigidly associated with the fixed part of a dental prosthesis. The device further comprises a female element defined by a prefabricated cap having an outwardly open seat. The cap is adapted to be rigidly associated with the removable part of a dental prosthesis, and the spherical male element is engageable, in snap-together engagement relationship, with the outwardly open seat, for associating the removable part of the prosthesis with the fixed part thereof.

14 Claims, 1 Drawing Sheet

COUPLING DEVICE FOR DENTAL PROSTHESES

This is a continuation application of application Ser. No. 07/064,481, filed June 22, 1987, now abandoned Apr. 5, 1990.

BACKGROUND OF THE INVENTION

The present invention relates to a coupling device for dental prostheses.

Removable dental prostheses, provided with adapted couplings or coupling devices for the rapid fixing of the prosthesis itself to the residual dental structures, are currently known.

A disadvantage encountered in the use of the known types of couplings for dental prostheses is that they do not permit the prosthesis to be easily and quickly substituted, as may be necessary, for example, in the event that the prosthesis is damaged.

Another disadvantage of the known types of couplings for dental prostheses is the fact that they are often only suitable for use with a specific type of prosthesis, thus constraining the dentist to store different types of couplings which are suitable for each different type of prosthesis.

An even further disadvantage of the known types of couplings for dental prostheses resides in the fact that they are frequently structurally complicated and expensive, and thus have an adverse affect on the overall cost of the installed dental prosthesis.

A not least disadvantage of the known types of couplings for dental prostheses is that they are very time-consuming to install, and require the exercise of great skill on the part of the dentist or dental surgeon.

SUMMARY OF THE INVENTION

Accordingly, an aim of the invention is to provide a coupling device for dental prostheses which permits a prosthesis to be easily and quickly substituted, as and when required, for example, in the event that the prosthesis is damaged.

Within the above-cited aim, an object of the invention is to provide a coupling device for dental prostheses which is versatile in that it can be used with different types of prostheses.

Another object of the invention is to provide a coupling device for dental prostheses, which is structurally simple and advantageous from a purely economical point of view.

A further object of the invention is to provide a coupling device for dental prostheses which can be very quickly and easily installed.

This aim and these and other objects which will become apparent hereinafter are achieved by the present coupling device for dental prostheses, characterized in that it comprises at least one substantially spherical male element, adapted for association with a fixed part of a prosthesis projecting from a gingiva region, said coupling device further comprising at least one female element, said female element being shaped complementarily with respect to said male element, adapted to be rigidly associated with a removable part of said prosthesis, and adapted to couple with said male element.

BRIEF DESCRIPTION OF THE DRAWINGS

Further features and advantages of the invention will become apparent from the description of a preferred embodiment of the coupling device for dental prostheses, illustrated only by way of a non-limiting example in the accompanying drawings, wherein.

DESCRIPTION OF THE PREFERRED EMBODIMENTS

With particular reference to the above described figures, the coupling device for dental prostheses comprises at least one male element 1, which is substantially spherical: the sphere of the element 1 is actually provided with two diametrically opposite flat regions 1a and 1b, the latter being the base connecting the male element to the member which supports it.

Figure 1:
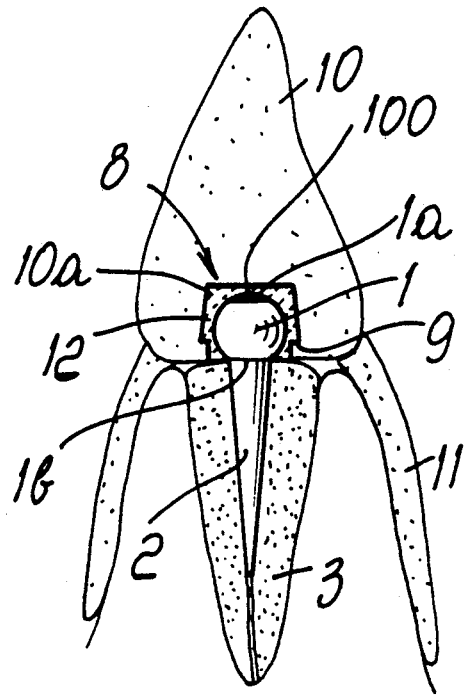

As illustrated in FIG. 1, said member is, by way of example, a prefabricated metallic reconstruction pin or intraradicular pin 2, which is particularly useful for installation in either temporary couplings or for being cemented in place, after being provided with suitable keying means such as notches (not illustrated), in the root 3 of a tooth which is not sufficiently valid.

If the root is to be considered as a valid part of the tooth reconstruction, it is convenient that the pin 2 with the male element 1 be obtained by means of an adapted casting starting from a pin, with its related male element, prefabricated in calcinable plastic material. In this case (FIG. 2), in the same casting a small cap 4 for covering the root, obtained starting from a small cap modelled in wax on said calcinable pin, is associated with the metallic pin 2 directly below the connecting base 1b.

Figure 4:
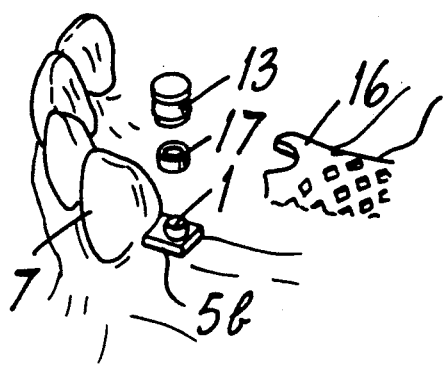
FIGS. 4 and 5 are exploded perspective views of respective steps of the preparation of prostheses using the coupling device according to the invention.
Figure 3:
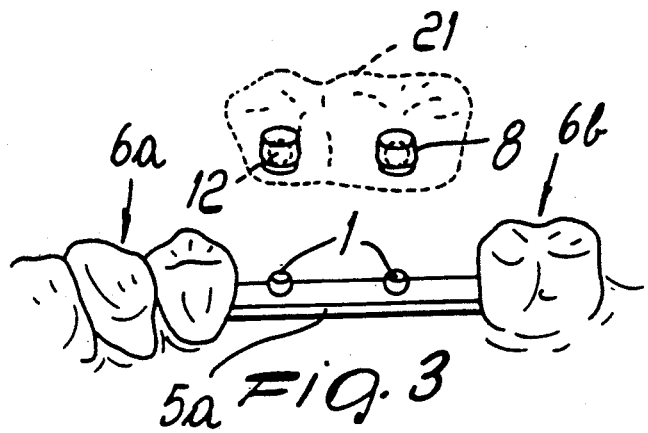
FIG. 3 is an exploded perspective view of a prosthesis using the same coupling device.
Figures 2A, 5:
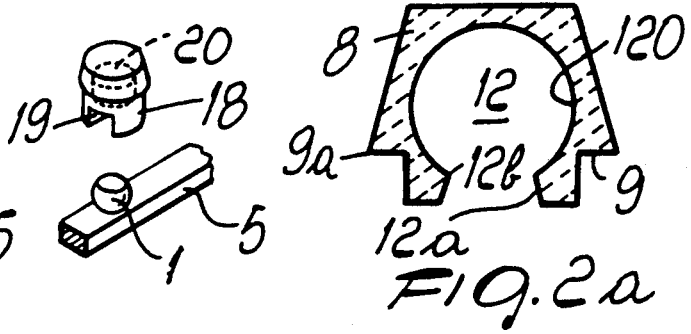
FIG. 2a is an enlarged cross-sectional detail view of the prefabricated cap of coupling device of FIGS. 1 and 2.

In FIGS. 3, 4 and 5, the member whereon the male element 1 is provided is a small bar, variably extended and generally indicated by the reference numeral 5: in FIG. 3 said member is constituted by a bar 5a which connects so-called pillars 6a and 6b, arranged mutually spaced apart, and is adapted to support two male elements 1; in FIG. 4 the bar 5b is very short and supports, next to an artificial crown 7, a single male element 1, defining an extracoronal coupling. In practice the small bars 5 may be obtained by means of suitable castings starting from prefabricated calcinable bars, arranged on a model, made of refractory coating, of the dental arch to be rehabilitated or reconstructed.

The male element 1 is therefore intended to be rigidly associated with a fixed part of a dental prosthesis, projecting from a region of the gingiva. Besides the applications already indicated and illustrated, the male element can be rigidly associated with engagement means such as screw threads, implanting blades and the like.

The coupling device furthermore comprises a female element which is shaped complementarily with respect to a corresponding male element 1, and is provided in the region of the gingiva in a removable part of a dental prosthesis and is thus intended to couple to said element 1.

This female element is expediently shaped like a sort prefabricated cap 8, advantageously made of plastic material or other elastically deformable material, and is intended to be accommodated and stably retained in said removable part of the prosthesis. In fact, in practice the small cap 8 is advantageously externally provided with a shoulder 9 and the corresponding seat 10a of the prosthesis is shaped complementary to its outer surface. In FIG. 1 said seat 10a is formed directly in the resin of an artificial crown 10 of a removable part 11 of a prosthesis, the small cap 8 being placed so as to constitute an insert of the removable part 11 during the preparation of the latter.

Figure 2:
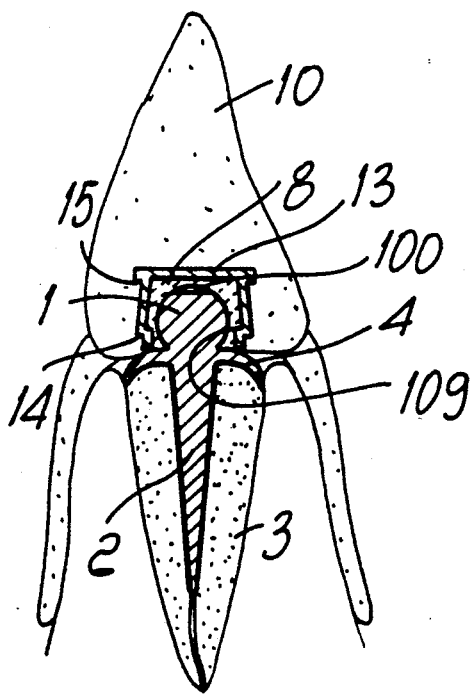
FIGS. 1 and 2 are front-to-back cross section views of respective prostheses incorporating the coupling device, according to the invention.

The male element 1 penetrates, by being pressed or force fitted, the recess 12 which is in the shape of a portion of a sphere and is formed in the cap 8, said recess 12 having an internal surface 120 (FIG. 2a) an entrance defined by a small stress raiser or lead-in zone 12a which is immediately followed by a narrow or neck-like portion 12b (FIG. 2a) of said recess 12: the coupling and, the uncoupling of the male element 1 and the essentially elastic small cap 8 occur in a snap-together manner. As shown in FIG. 2, when the male element 1 is force-fitted into the cap 8, a recess 100 is defined between the internal surface of the recess 8 and the flat region 1a of the male element 1.

In any case, it may be preferred that the seat 10a for the accommodation and the stable retention of the prefabricated cap 8 be defined in a metallic part. In FIG. 2 said metallic part is in the form of a prefabricated case 13, the internal surface whereof is shaped complementary to the outer surface of the plastic cap 8 and as, clearly illustrated in FIG. 2, has an internal shoulder 109. The cap 8, which tapers inwardly from the outer edge 9a of the shoulder 9, is thus facilitated in its entry into the case 13, wherein it couples in snap-together engagement relationship through engagement of the shoulders 9, 109, without being able to come out of the case 13 except by being damaged or destroyed. In order to constitute a non-removable insert of the artificial crown, the metallic case 13 is expediently provided with external shoulders 14 and 15.

As illustrated in FIG. 4, the metallic prefabricated case 13 can however be welded to the skeletal structure 16 of a skeletal prosthesis. For exact positioning, during welding of the case 13 to the skeletal structure 16, the case 13 is advantageously mounted on the related male element 1 by means of a small ring in plastic material 17, which permits said male element 1 to be temporarily associated with the case 13 without the occurrence of a stable snap-together retention as occurs between the prefabricated caps 8 and the case 13 of the coupling device of FIGS. 1 and 2.

As well as by means of a small cap 13, the seat in a metallic case 13 adapted for accommodating the plastic cap 8 can be obtained, for example, by means of an adapted lost-wax casting starting from a model, in refractory coating, of the arch to be reconstructed or rehabilitated. In this case the model of the arch reproduces the fixed part of the prosthesis and the male elements 1 thereof, to said elements there being coupled the respective small plastic caps 8. Better still, when dealing with elements 1 on small bars 5, a metallic element 18 (FIG. 5) may be provided on the element 1 and has substantially the same outer shape as the plastic cap 8: the element 18 expediently downwardly defines a saddle-like conformation including a slot 19 and is placed astride the bar 5, the diametral slot 19 accommodating a portion of the bar 5. A seat 20, formed at the interior of the element 18, is expediently cylindrical with a diameter which is substantially equal to the diameter of the sphere of the male element 1.

By casting it is possible to achieve, in the removable part 21 of the prosthesis of FIG. 3, metallic cases for accommodating the plastic caps 8.

It should be noted that the retention and the encircling, provided by metallic seats (for example, as defined by the small case 13) on the plastic caps 8, ensure a safe and durable stability of the couplings between male elements 1 and caps 8 without thereby limiting the removal of the movable parts of prostheses.

Obviously the invention is susceptible to modifications and adaptions, without thereby departing from the purview of the instant inventive concept.

Furthermore, any suitable materials, dimensions and contingent shapes may be used according to requirements.

We claim:

1. Coupling device for dental prostheses comprising in combination at least one male element and at least one female element, said female element comprising;
   at least one prefabricated case made of rigid material,
   a plurality of external shoulders formed on said prefabricated case for rigidly associated said case with a dental prosthesis,
   at least one inwardly protruding shoulder formed on said case,
   at least one cap, said cap being made of elastically deformable material and inserted into said prefabricated case,
   at least one shoulder defined externally no said cap, said at least one shoulder engaging said inwardly protruding shoulder formed on said case for retaining said cap within said case,
   a substantially spherical recess formed inside said cap, an internal surface defined by said spherical recess,
   an inwardly narrowing lead-in zone communicating with said substantially spherical recess, and
   at least one inwardly protruding neck-like portion defined on said cap between said substantially spherical recess and said lead-in zone,
   said male element comprising;
   at least one substantially spherical element, said spherical element being rigidly associable with a fixed part of a prosthesis and inserted into said substantially spherical recess, and
   at least two substantially diametrically opposite flat regions formed on said spherical element,
   wherein at least one cavity is defined between at least one of said flat regions and said internal surface of said spherical recess.

2. Coupling device for dental prostheses according to claim 1, wherein said at least one shoulder defined externally on said cap has an outer edge, and wherein said cap has at least one linear tapered portion, said at least one linear tapered portion tapering inwardly from said outer edge of said at least one shoulder for facilitating force-fitting of said cap into said prefabricated case.

3. Coupling device for dental prostheses according to claim 1, wherein at least one of said diametrically opposite flat regions defines a base, said base being connected to said fixed part of said prostheses.

4. Coupling device for dental prostheses according to claim 3, wherein said fixed part of said prosthesis is constituted by at least one intraradicular pin.

5. Coupling device for dental prostheses according to claim 3, wherein said fixed part of said prosthesis is constituted by at least one bar, said bar being connectable to pillars.

6. Coupling device for dental prostheses according to claim 3, wherein said fixed part of said prosthesis is constituted by at least one bar, and wherein at least one of said diametrically opposite flat regions is traversed by at least one slot, said slot defining at least one saddle-like conformation, said saddle-like conformation being located astride said bar, said bar being connectable to pillars.

7. Coupling device for dental prostheses according to claim 1, further comprising at least one ring, said ring being temporarily interposed between said predetermined case and said spherical element before insertion of said cap into said prefabricated case, for effecting exact positioning of said prefabricated case.

8. Coupling device for dental prostheses according to claim 7, wherein said prefabricated case is fixed to a prosthesis skeletal structure.

9. In a coupling device for dental prostheses, a female element according to claim 7, wherein said at least one shoulder has an outer edge, and wherein said cap has at least one linear tapered portion, said at least one linear tapered portion tapering inwardly from said outer edge of said at least one shoulder for facilitating force-fitting of said cap into said prefabricated case.

10. In a coupling device for dental prostheses, a female element according to claim 7 further comprising at least one ring, said ring being temporarily interposed between said prefabricated case and said spherical element before insertion of said cap into said prefabricated case, for effecting exact positioning of said prefabricated case.

11. In a coupling device for dental prostheses, a female element according to claim 10 wherein said prefabricated case is fixed to a prosthesis skeletal structure.

12. In a coupling device for dental prostheses, a female element comprising;
    at least one prefabricated case made of rigid material,
    a plurality of external shoulders formed on said prefabricated case for rigidly associating said case with a dental prosthesis,
    at least one inwardly protruding shoulder formed on said case,
    at least one cap, said cap being made of elastically deformable material and inserted into said prefabricated case,
    at least one shoulder defined externally on said cap, said at least one shoulder engaging said inwardly protruding shoulder formed on said case for retaining said cap within said case,
    a substantially spherical recess formed inside said cap,
    an internal surface defined by said spherical recess,
    an inwardly narrowing lead-in zone communicating with said substantially spherical recess, and
    at least one inwardly protruding neck-like portion defined on said cap between said substantially spherical recess and said lead-in zone,
    wherein said female element is adapted for having defined therein at least one cavity located between said internal surface of said substantially spherical recess and at least one flat region formed on a substantially spherical male element, upon said male element being inserted into said female element.

13. In a coupling device for dental prostheses, a male element comprising;
    at least one substantially spherical element, said spherical element being rapidly associable with a fixed part of a prostheses, and
    at least two substantially diametrically opposite flat regions formed on said spherical element, wherein said male element is adapted for defining at least one cavity between at least one of said flat regions and an inner surface of a substantially spherical recess defined within a prefabricated case of a female element when said male element is inserted into said prefabricated case, said male element further comprising at least one ring, said ring being temporarily interposable between said prefabricated case and said spherical element before insertion of said male element into said prefabricated case, for effecting exact positioning of said prefabricated case.

14. In a coupling device for dental prostheses, a male element according to claim 13, wherein said prefabricated case is fixed to a prosthesis skeletal structure.

* * * * *